(12) United States Patent
Molenaar et al.

(10) Patent No.: US 7,531,516 B2
(45) Date of Patent: May 12, 2009

(54) PEPTIDIC COMPOUNDS SELECTIVELY BINDING TO P-SELECTIN

(75) Inventors: Thomas Jacobus Maria Molenaar, Leiden (NL); Johan Kuiper, Gouda (NL); Theodorus Josephus Cornelis Van Berkel, Haarlem (NL); Erik Anna Biessen, Leiden (NL)

(73) Assignee: Astellas Pharma Europe B.V., Leiderdorp (NL)

( * ) Notice: Subject to any disclaimer, the term of this patent is extended or adjusted under 35 U.S.C. 154(b) by 0 days.

(21) Appl. No.: 10/488,509

(22) PCT Filed: Aug. 28, 2002

(86) PCT No.: PCT/NL02/00566

§ 371 (c)(1),
(2), (4) Date: Mar. 2, 2004

(87) PCT Pub. No.: WO03/020753

PCT Pub. Date: Mar. 13, 2003

(65) Prior Publication Data

US 2005/0004035 A1    Jan. 6, 2005

(30) Foreign Application Priority Data

Sep. 3, 2001   (EP) .................................. 01203314

(51) Int. Cl.
| | |
|---|---|
| *A61K 38/00* | (2006.01) |
| *A61K 38/08* | (2006.01) |
| *A61K 38/10* | (2006.01) |
| *A61K 38/16* | (2006.01) |
| *C07K 7/00* | (2006.01) |
| *C07K 7/06* | (2006.01) |
| *C07K 7/08* | (2006.01) |
| *C07K 14/00* | (2006.01) |

(52) U.S. Cl. .......................... 514/16; 530/300; 530/326; 530/327; 530/328; 530/329; 514/2; 514/13; 514/14; 514/15

(58) Field of Classification Search ........................ None
See application file for complete search history.

(56) References Cited

U.S. PATENT DOCUMENTS

| 5,663,144 A | * | 9/1997 | Greene et al. ................. 514/14 |
| 2002/0152495 A1 | * | 10/2002 | Ito et al. ..................... 800/278 |

FOREIGN PATENT DOCUMENTS

| WO | WO 94/05269 A | | 3/1994 |
| WO | WO 94/14836 A | | 7/1994 |
| WO | WO 95/31210 A | | 11/1995 |
| WO | WO 96/00581 | * | 1/1996 |
| WO | WO 00/34303 A | | 6/2000 |

OTHER PUBLICATIONS

Berg et al. Cloning and Characterization of a Novel B Integrin-Related cDNA Coding for the Protein TIED ("Ten B Integrin EGF-like Repeat Domains") That Maps to Chromosome Band 13q33: A Divergent Stand-Alone Integrin Stalk Structure. Genomics 1999, vol. 56, pp. 169-178.*

Kaneko et al. The Plasminogen Activator Inhibitor-1 Binding Site in the Kringle-2 Domain of Tissue-Type Plasminogen Activator. Biochemical and Biophysical Research Communications. 1991. vol. 178, No. 3, pp. 1160-1166.*

* cited by examiner

*Primary Examiner*—Cecilia Tsang
*Assistant Examiner*—Julie Ha
(74) *Attorney, Agent, or Firm*—McDonnell Boehnen Hulbert & Berghoff LLP

(57) ABSTRACT

The present invention relates to compounds which bind selectively to the adhesion molecule human P-selectin, and particularly to such compounds comprising a peptide with an amino acid sequence $XA_xA_3A_1A_2A_1Y$, or a functional equivalent of said peptide. In addition, the invention relates to methods for preparing such compounds, to the use of such compounds in therapeutic or diagnostic methods and in pharmaceutical compositions, to nucleic acids encoding for proteinaceous materials comprising the amino acid sequences of said compounds, to gene delivery vehicles comprising such nucleic acids, to binding molecules binding to said compounds, and to a method for determining whether a compound is capable of binding to P-selectin.

22 Claims, No Drawings

SEQUENCE LISTING

```
<160> NUMBER OF SEQ ID NOS: 19

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

Asn Val Val Glu Cys
1               5

<210> SEQ ID NO 2
<211> LENGTH: 5
<212> TYPE: PRT
<213> ORGANISM: Artificial
<220> FEATURE:
<223> OTHER INFORMATION: Synthetic

<400> SEQUENCE: 2

Gly Phe Val Glu Cys
1               5

<210> SEQ ID NO 3
<211> LENGTH: 17
<212> TYPE: PRT
<213> ORGANISM: Artificial
<220> FEATURE:
<223> OTHER INFORMATION: Synthetic

<400> SEQUENCE: 3

Cys Pro Glu Phe Val Asp Val Glu Gly Asp Pro Gly Ala Leu Leu Ala
1               5                   10                  15

Cys

<210> SEQ ID NO 4
<211> LENGTH: 17
<212> TYPE: PRT
<213> ORGANISM: Artificial
<220> FEATURE:
<223> OTHER INFORMATION: Synthetic

<400> SEQUENCE: 4

Cys Gly Trp Val Asp Val Ile Ala Ser Gly Asp Thr Ala Thr Leu Ala
1               5                   10                  15
```

Cys

<210> SEQ ID NO 5
<211> LENGTH: 17
<212> TYPE: PRT
<213> ORGANISM: Artificial
<220> FEATURE:
<223> OTHER INFORMATION: Synthetic

<400> SEQUENCE: 5

Cys Asp Val Glu Trp Val Asp Val Ser Ser Leu Glu Trp Asp Leu Pro
1               5                   10                  15

Cys

<210> SEQ ID NO 6
<211> LENGTH: 17
<212> TYPE: PRT
<213> ORGANISM: Artificial
<220> FEATURE:
<223> OTHER INFORMATION: Synthetic

<400> SEQUENCE: 6

Cys Pro Asp Trp Val Asp Val Phe Lys Leu Val Glu Gly Val Met Leu
1               5                   10                  15

Cys

<210> SEQ ID NO 7
<211> LENGTH: 17
<212> TYPE: PRT
<213> ORGANISM: Artificial
<220> FEATURE:
<223> OTHER INFORMATION: Synthetic

<400> SEQUENCE: 7

Cys Leu Met Gly Cys Trp Cys Asp Val Gly Val Gly Gly Glu Ser Leu
1               5                   10                  15

Cys

<210> SEQ ID NO 8
<211> LENGTH: 15
<212> TYPE: PRT
<213> ORGANISM: Artificial
<220> FEATURE:
<223> OTHER INFORMATION: Synthetic

<400> SEQUENCE: 8

Val Gly Leu Asp Pro Arg Asp Trp Val Asp Val Ser Asp Tyr Ala
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic

<400> SEQUENCE: 9

Asp Trp Val Asp Val Arg Glu Val Leu Thr Gly Glu Gln Arg Val
1               5                   10                  15

<210> SEQ ID NO 10
<211> LENGTH: 10
<212> TYPE: PRT
<213> ORGANISM: Artificial

```
<220> FEATURE:
<223> OTHER INFORMATION: Synthetic

<400> SEQUENCE: 10

Cys Asp Val Glu Trp Val Asp Val Ser Cys
1               5                   10

<210> SEQ ID NO 11
<211> LENGTH: 9
<212> TYPE: PRT
<213> ORGANISM: Artificial
<220> FEATURE:
<223> OTHER INFORMATION: Artificial

<400> SEQUENCE: 11

Cys Asp Val Glu Trp Val Asp Val Ser
1               5

<210> SEQ ID NO 12
<211> LENGTH: 8
<212> TYPE: PRT
<213> ORGANISM: Artificial
<220> FEATURE:
<223> OTHER INFORMATION: Synthetic

<400> SEQUENCE: 12

Asp Val Glu Trp Val Asp Val Ser
1               5

<210> SEQ ID NO 13
<211> LENGTH: 8
<212> TYPE: PRT
<213> ORGANISM: Artificial
<220> FEATURE:
<223> OTHER INFORMATION: Synthetic

<400> SEQUENCE: 13

Asp Val Glu Trp Val Asp Val Ala
1               5

<210> SEQ ID NO 14
<211> LENGTH: 8
<212> TYPE: PRT
<213> ORGANISM: Artificial
<220> FEATURE:
<223> OTHER INFORMATION: Synthetic

<400> SEQUENCE: 14

Asp Val Glu Ala Val Asp Val Ser
1               5

<210> SEQ ID NO 15
<211> LENGTH: 8
<212> TYPE: PRT
<213> ORGANISM: Artificial
<220> FEATURE:
<223> OTHER INFORMATION: Synthetic

<400> SEQUENCE: 15

Asp Val Glu Trp Ala Asp Val Ser
1               5

<210> SEQ ID NO 16
<211> LENGTH: 8
<212> TYPE: PRT
<213> ORGANISM: Artificial
<220> FEATURE:
```

```
<223> OTHER INFORMATION: Synthetic

<400> SEQUENCE: 16

Asp Val Glu Trp Val Ala Val Ser
1               5

<210> SEQ ID NO 17
<211> LENGTH: 8
<212> TYPE: PRT
<213> ORGANISM: Artificial
<220> FEATURE:
<223> OTHER INFORMATION: Synthetic

<400> SEQUENCE: 17

Asp Val Glu Trp Val Asp Ala Ser
1               5

<210> SEQ ID NO 18
<211> LENGTH: 6
<212> TYPE: PRT
<213> ORGANISM: Artificial
<220> FEATURE:
<223> OTHER INFORMATION: Synthetic

<400> SEQUENCE: 18

Glu Trp Val Lys Val Ala
1               5

<210> SEQ ID NO 19
<211> LENGTH: 5
<212> TYPE: PRT
<213> ORGANISM: Artificial
<220> FEATURE:
<223> OTHER INFORMATION: Synthetic

<400> SEQUENCE: 19

Glu Trp Val Asp Val
1               5
```

PEPTIDIC COMPOUNDS SELECTIVELY BINDING TO P-SELECTIN

FIELD OF THE INVENTION

The present invention relates to compounds which bind selectively to the adhesion molecule human P-selectin, to methods for preparing such compounds, to the use of such compounds in therapeutic or diagnostic methods and in pharmaceutical compositions, to nucleic acids encoding for proteinaceous materials comprising the amino acid sequences of said compounds, to gene delivery vehicles comprising such nucleic acids, to binding molecules binding to said compounds, and to a method for determining whether a compound is capable of binding to P-selectin.

BACKGROUND OF THE INVENTION

In recent years, cell surface adhesion molecules have become recognized as key mediators in numerous cellular processes including cell growth, differentiation, immune cell transmigration and response, and cancer metastasis. Four major categories of adhesion molecules have been identified: The immunoglobulin superfamily cell adhesion molecules (CAMs), cadherins, integrins, and selecting. The selectins represent a family of presently three transmembraneous, carbohydrate-binding glycoproteins: "endothelial" E-selectin, "leukocyte" L-selectin, and "platelet" P-selectin. All three selectins are divalent cation (e.g. calcium) dependent and possess an extracellular domain with a carbohydrate recognition motif, an epidermal growth factor-like motif, and some smaller domains related to complement-regulatory proteins.

Human P-selectin (also referred to as GMP-140, LECAM-3, PADGEM, CD62, CD62P) is expressed by platelets and endothelial cells. When expressed on the surfaces of these cells, its most notable effect is the slowing of leukocytes as these leave the capillaries and enter the postcapillary venules, the latter representing the major site of leukocyte-endothelium adhesion. The slowing process is observed as leukocyte rolling, signifying an initial adhesion with relatively low affinity. The firm adhesion of rolling leukocytes is primarily mediated by integrins.

In endothelial cells, P-selectin is stored on Weibel-Palade bodies; in platelets, it is found in the α-granules. Following activation, P-selectin is mobilized to the cell surfaces within a few minutes in response to a variety of inflammatory or thrombogenic agents. The endothelial P-selectin's primarily function is to recruit leukocytes into postcapillary venules, while platelet P-selectin also results in the formation of thrombi. One of the presently known natural ligands of P-selectin is PSGL-1 (P-selectin glycoprotein ligand-1), a 160 kDa sialoprotein expressed on the surface of leukocytes where it is concentrated at the uropod. More detailed descriptions of the structure and functions of p-selectin are found in numerous publications, such as J. Panes, Pathophysiology 5, 271 (1999); F. Chamoun et al., Frontiers in Bioscience 5, e103 (Nov. 1, 2000); S.-I. Hayachi, Circulation 102, 1710 (2000).

P-selectin also appears to be involved more directly in platelet aggregation, as was shown recently by studies of the Ca-independent interactions of P-selectin with 3-sulfated galactosyl ceramide (also referred to as sulfatides). This interaction probably takes place at a different binding site of P-selectin, as the binding can be inhibited by the antibody WASP12.2, but not by AK4, whereas the binding of the natural P-selectin ligand PSGL-1, which is involved in leukocyte adhesion, is blocked by both WASP12.2 and AK4. However, it appears that the binding sites are overlapping. It is assumed that sulfatide interactions stabilize platelet aggregates.

Inflammation and inflammatory processes play a major role in the pathophysiology of numerous diseases and conditions. Conditions of the brain in which increased selectin levels were found, and which may therefore involve selectin-mediated pathophysiological events, include severe traumatic brain injury, relapsing-remitting multiple sclerosis, cerebral artery occlusion, ischemia, and stroke. Conditions of the heart in which selectins are suggested to play a role include acute myocardial infarct, arterial injury, such as produced by angioplasty, and ischemia. Similarly, selectins are involved in conditions of the kidneys, such as renal injury from ischemia and reperfusion, and renal failure. Furthermore, selectins appear to play a role in organ transplant rejection, cold ischemia, hemorrhagic shock, septic shock, tumor metastasis, chronic inflammation, rheumatoid arthritis, inflammatory bowel disease, atherosclerosis, restenosis, angiogenesis, disseminated intravascular coagulation, adult respiratory stress syndrome, and circulatory shock.

Thus, it would seem feasible to improve these and other conditions involving the activation of endothelial cells and leukocytes and specifically the mobilization and expression of P-selectin by specifically interrupting the P-selectin cascades. This can be done, for instance, by the administration of ligands which selectively bind to human P-selectin, but which do not possess its bioactivity. By this method, mobilized P-selectin could be inactivated and leukocyte-induced tissue damage prevented. Potentially, the same effect could be achieved by gene therapy, provided the P-selectin ligand or antagonist is a peptide or modified peptide. According to this method, somatic cells of a person in need of the therapy would be transfected with an expression vector carrying a DNA sequence encoding a P-selectin antagonist.

P-selectin ligands or antagonists may also be used for the prevention of diseases and conditions described above. Furthermore, such ligands may also be useful in the in vivo or in vitro diagnosis of these diseases.

Various attempts have been made in recent years to identify or create such selective ligands to P-selectin. So far, a number of substances were tested, but no clinical studies have yet provided conclusive evidence that any of these compounds produce the desired clinical effects while being tolerable in terms of side effects.

For instance, antibodies to P-selectin that were produced and tested in animal models, were found to protect kidneys from ischemic-reperfusion injury (H. C. Rabb et al., JASN 5, 907, 1997; U.S. Pat. No. 6,033,667). In another study, a recombinant soluble form of P-selectin glycoprotein ligand-1 (rPSGL-Ig) was used to inhibit thrombosis in cats (M. J. Eppihimer et al., Arteriosclerosis, Thrombosis, and Vascular Biology 20, 2483, 2000). WO-A-96/09309 discloses oligosaccharide structures that are ligands to E- and P-selectin. WO-A-99/41363 discloses podocalyxin-like proteins that bind to selectins. WO-A-00/41711 describes various smaller peptides or peptide sequences that bind to members of the human selectin family; most of the sequences comprise one or more units of leucine or isoleucine.

As another approach to inhibit the P-selectin cascade, various peptides derived from the lectin domain of the selectin family were found to inhibit neutrophil adhesion to P-selectin (e.g. U.S. Pat. No. 6,111,065 and U.S. Pat. No. 5,916,876); these peptides probably bind to P-selectin receptors on leukocytes.

In WO-A-94/05269, peptides are described which inhibit binding of selectins such as P-selectin, E-selectin and L-selectin. These peptides have as their core region portions of the 11-18 amino acid sequence of P-selectin, E-selectin or L-selectin. Further, WO-A-95/31210 relates to peptides and compounds that bind selectins including endothelium leukocyte adhesion molecule 1 (ELAM-1). These peptides are used for blocking adhesion of leukocytes to the selecting, i.e. especially E-selectin, but also P-selectin or L-selectin, for the purpose of inhibiting inflammation.

Despite these efforts, there is still a need for substances with selective affinity to P-selectin, which can be used for preparing pharmaceutical compositions for the diagnosis, prevention and treatment of various diseases and conditions involving the adherence of leukocytes to vascular endothelial cells or to platelets. There is also a need for P-selectin ligands, which can be used as targeting molecules or moieties in pharmaceutical compositions for the targeting of drugs or genetic material to tissues expressing P-selectin.

OBJECTS OF THE INVENTION

It is therefore an object of the invention to provide compounds with affinity to human P-selectin.

In particular, it is an object of the invention to provide compounds which act as antagonists or partial antagonists of P-selectin.

It is another object of the invention to provide compounds which act as targeting ligands with an ability to target drugs and genetic material to cells and tissues expressing P-selectin.

A further object of the invention is the presentation of methods for preparing such compounds.

Yet another object is the presentation of uses of such compounds, and of compositions which contain the compounds.

Other objects of the present invention will become clear on the basis of the following description.

SUMMARY OF THE INVENTION

In a first aspect, the present invention provides compounds with selective affinity to human P-selectin. The compounds of the invention are peptides or functional equivalents, such as modified peptides, peptide analogues, or peptidomimetics. They comprise the sequence $XA_xA_3A_1A_2A_1Y$, wherein $A_1$ is a D- or L-amino acid selected from the group consisting of cysteine (C), methionine (M), and valine (V), or an analogue or mimetic thereof; $A_2$ is a D- or L-amino acid selected from the group consisting of aspartic acid (D) or an analogue or mimetic thereof; and $A_3$ is a D- or L-amino acid selected from the group consisting of phenylalanine (F), tyrosine (Y), and tryptophan (W), or an analogue or mimetic thereof; $A_x$ is any D- or L-amino acid or an analogue or mimetic thereof; X is any N-terminal group or sequence; and Y is any C-terminal group or-sequence. The compounds have an affinity constant to human P-selectin typically in the micromolar range, but their affinity is increased substantially when they are configured as multimers with a valency of 2 or more.

In WO-A-00134303, a 610 amino acids containing sequence is described which comprises the sequences Asn-Val-Val-Glu-Cys (NVVEC) (SEQ ID No: 1) and Gly-Phe-Val-Glu-Cys (GFVEC) (SEQ ID No: 2). P-selectin is not mentioned in this WO-A-00134303. The two sequences given are not analogues or mimetics of compounds of the present invention.

In a second aspect, the invention provides methods for the preparation of such compounds. The methods include the chemical and enzymatic ligation of amino acids monomers or oligomers to assemble the compounds. They also include the expression of nucleic acid sequences encoding the compounds in host cells, using a vector for transfecting the host cells with the nucleic acid sequences.

In a further aspect, the invention relates to the use of the compounds of the invention for preparing pharmaceutical or diagnostic compositions which are suitable for inhibiting the binding of leukocytes to platelets and endothelial cells in vitro and in vivo as well as for the direct inhibition of platelet aggregation. As medicaments, the compositions may be useful in the treatment and prevention of conditions and disorders which involve the activation of P-selectin-mediated binding of leukocytes to platelets and endothelial cells, such as thrombotic disorders, ischemia, restenosis, atherosclerosis, renal failure, parasitic diseases, tumors and tumor metastases; furthermore, the compounds and the compositions may be useful in the diagnosis, prevention and therapy of diseases and conditions involving platelet aggregation, such as thrombosis, stroke and heart attacks. Pharmaceutical compositions containing the compounds of the invention may be adapted for various routes of administration, such as parenteral, oral, transmucosal, nasal, or pulmonary. They may further contain drug targeting agents, bioavailability enhancement agents, or active ingredients other than compounds of the invention, and provide for immediate or modified release.

In yet a further aspect, the present invention relates to a method for determining whether a molecule comprises a binding affinity for P-selectin, comprising contacting of P-selectin or a functional equivalent thereof with said molecule and with a compound according to the invention, followed by determining whether binding of said compound to said P-selectin or functional analogue thereof is reduced.

Further, the invention relates to a nucleic acid encoding a proteinaceous molecule comprising an amino acid sequence $XA_xA_3A_1A_2A_1Y$, wherein $A_x$, $A_3$, $A_1$ and $A_2$ are defined as herein-above and wherein X is the N-terminal side of said sequence and Y is the C-terminal side of said sequence, or a functional equivalent thereof. As used herein, proteinaceous molecules are compounds based on amino acid sequences, such as proteins and oligo—or polypeptides, and derivatives or analogues thereof The said nucleic acid can be used for the preparation of a medicament, while in addition gene delivery vehicles comprising said nucleic acid are also within the scope of the present invention.

In a further aspect, the present invention also encompasses binding molecules which are capable of specifically binding a compound of the invention.

Furthermore, the present invention relates to a method for determining whether a compound is capable of binding to human P-selectin, comprising substituting in a compound according to the invention, an amino acid for a conservative amino acid and determining whether the resulting compound is capable of binding to said P-selectin.

DETAILED DESCRIPTION OF THE INVENTION

The compounds of the invention have an affinity to human P-selectin, a membrane glycoprotein expressed by vascular endothelial cell and platelets, which is involved in leukocyte adhesion to the endothelium and platelets. The affinity or binding characteristics of compounds to P-selectin can be quantified, for example, in terms of the affinity constant ($IC_{50}$). Typically, an affinity constant of about 50-100 µM or less would be considered as evidence for affinity and binding. More desirable for ligands are substances with affinity constants of about 10 µM or less. The highest affinity constants attainable for the non-covalent type bonds playing a role in the interactions or bindings in accordance with the present invention is about $10^{-15}$ M. Generally, however, the affinity constants are higher than about $10^{-12}$ M and in most cases higher than about $10^{-9}$ M.

Furthermore, a compound of the invention comprises a peptide or a molecular structure that is related to a peptide, herein referred to as functional equivalent.

Peptides are defined as amides that are derived from two or more amino acids by combination of the amino group of one acid with the carboxyl group of another (Merriam Webster Medical Dictionary© 2001). As used herein, a peptide may also refer to a peptidic structure within a molecule. Typically, peptides are composed of naturally occurring L-α-amino acids, which are alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K) methionine (Met or M), phenylalanine (Phe or F), proline (Pro or P), serine (Ser or S), threonine (Thr or T), tryptophan (Trp or W), tyrosine (Tyr or Y), and valine (Val or V).

Functional equivalents of the peptides of the invention are proteinaceous molecules, comprising the same human P-selectin binding activity in kind, but not necessarily in amount, and may, for instance, be modified peptides, peptoids, peptide analogues or peptidomimetics.

Modified peptides are molecules derived from peptides by the introduction of substituents or functional groups which are not present in naturally occurring amino acids. The term also includes compounds which are obtained by the reaction of peptides with molecules from other chemical categories, whether these molecules a naturally occurring or not. For instance, biotinylated peptides, glycoproteins, and lipoproteins are frequently found in nature, while peptides modified with polyethylene glycol, such as pegylated interferon α-2b (Peg-Intron®), are examples of chemically modified peptides that have been designed to alter some, but not all of the peptides' properties.

Peptoids, like peptides, are typically amides of two or more amino acids. However, they are frequently not directly derived from naturally occurring amino acids, but rather of various types of chemically synthesized L- or D-amino acids.

Peptidomimetics, in their broadest scope, are compounds which are in their functional structure more or less similar to a peptide, but which may also contain non-peptidic bonds in the backbone, or D-amino acids. In general, peptidomimetics serve as substitutes for native peptides in the interaction with receptors and enzymes (Pharmaceutical Biotechnology, Ed. D. J. A. Crommelin and R. D. Sindelar, Harwood Academic Publishers, 1997, p. 138). Pseudopeptides, a class of peptidomimetics, are compounds containing amide bond isosteres instead of amide bonds (ibid., pp. 137-140).

Compounds of the invention also include salts of peptides or functional equivalents, such as pharmaceutically acceptable acid- or base addition salts. They also include multimers of peptides or functional equivalents.

The compounds of the invention are characterized in that they comprise the sequence $XA_xA_3A_1A_2A_1Y$, wherein $A_1$ is a D- or L-cysteine (C), D- or L-methionine (M), D- or L-valine (V) or an analogue thereof; $A_2$ is a D- or L-aspartic acid (O) or an analogue thereof; $A_3$ is a D- or L- phenylalanine (F), D- or L-tyrosine (Y) or D- or L-tryptophan (W) or an analogue thereof; $A_x$ is a D- or L-amino acid, and wherein X marks the N-terminal side of said sequence and Y marks the C-terminal side of said sequence or wherein X and Y together can form a cyclic system. More particularly, X is a hydrogen or a residue comprising 1 to 6 D- or L-amino acids; Y is a hydroxyl or a residue comprising 1 to 11 D- or L-amino acids terminated by a hydroxyl.

According to the invention, the two units of $A_1$ within the sequence are selected independently; they can be identical or different from each other. Preferably, at least one of the $A_1$ units represents valine (V). More preferably, both $A_1$ units are valine (V). In another embodiment, $A_1$ is an analogue or mimetic of cysteine (C), methionine (M), or valine (V). Techniques for selecting appropriate analogues or mimetics of naturally occurring amino acids are well-known to those skilled in the art. For example, the pseudopeptide approach aims at achieving a higher chemical or enzymatic stability of a peptide while retaining its bioactivity. Peptide bonds which undergo rapid degradation in vivo are replaced by other functional groups to create bioisosteres or amide bond surrogates. Examples of bioisosteric groups are N-methyl amide, thioester, thioamide, ketomethylene, methyleneamino, retro-inverse amide, methylenethio, and methyleneoxy groups (ibid., pp. 138-139). An approach to improve the selectivity of a peptide is to introduce conformational constraints to the backbone, which decreases the number of potential receptor or enzyme interactions. The constraints are most often achieved by the introduction of carbon-carbon double bonds (olefinic analogues) and ring structures (ibid.). A further method to identify analogues which mimic the functional structure of an amino acid such as cysteine (C), methionine (M), or valine (V) is computer-aided modeling. Preferred mimetic structures possess a side chain with similar charge or electronegativity, hydrophobicity and spatial orientation to said amino acids. In another embodiment, one or both $A_1$ units are D-amino acid analogues of cysteine (C), methionine (M), or valine (V).

As said, the present invention also encompasses functional equivalents of the said peptides. Equivalents can, among others, be found by amino acid substitution using conservative amino acid changes. Particularly, the invention also encompasses a method for determining whether a compound is capable of binding to human P-selectin, comprising substituting in a compound according to the invention, an amino acid for a conservative amino acid and determining whether the resulting compound is capable of binding to said P-selectin. In this light, it has been found, and is also part of the present invention, that the precise amino acid composition of the peptide becomes—at least for the amino acids $A_2$ and $A_3$—somewhat less critical with increasing numbers of amino acids in the peptide. For instance, it has been found that a peptide, comprising more than 10 and preferably more than 12 amino acids, that comprises phenylalanine (F) instead of tryptophan (W) as $A_3$, is capable of specifically binding to human P-selectin. Yet, when the peptide comprises 6 amino acids, said substitution of tryptophan by phenylalanine does not lead to a specifically binding peptide. Another example of an equivalent in accordance with the present invention is a peptide comprising an amino acid sequence $XA_xA_3A_1A_2A_1Y$ and comprising 15 amino acids comprising a glutamic acid (E) at position $A_2$ instead of aspartic acid (D) and which gives a specific P-selectin binding. However, when the peptide chain is only 6 amino acids, the same substitution does not give a specific binding peptide. For example, the sequence EWVEVA has a binding affinity of 1,600 µM, while a 15-mer having said sequence has a binding affinity of less than 10 µM. Without wishing to be bound by any theory, it is assumed that the effect of the length of the peptide is related to the conformation of the peptide, which has an impact on the binding capacity. When the peptides of the present invention are at least decamers or, preferably at least dodecamers, $A_3$ and $A_2$ may represent F and E, respectively.

According to the invention, $A_2$ is a D- or L-amino acid with a solvent exposed side chain bearing a negative charge at physiological pH, selected from the group consisting of aspartic acid (D) and glutamic acid (E), or an analogue or mimetic thereof. In preferred embodiments, $A_2$ is either L-glutamic acid (E) or L-aspartic acid (D). In other embodiments, $A_2$ is an analogue structure related to aspartic acid (D) or glutamic acid (E). For identifying appropriate analogues, the same principles apply as those that have been set forth with regard to $A_1$.

$A_3$ is a D- or L-amino acid with an aromatic side chain selected from the group consisting of phenylalanine (F), tyrosine (Y), and tryptophan (W), or an analogue or mimetic thereof More preferably, $A_3$ is an L-amino acid selected from this group. Most preferred is tryptophan (W). In other embodiments, $A_3$ is an analogue structure related to phenylalanine (F), tyrosine (Y), or tryptophan (W) as defined above.

$A_x$ can be any D- or L-amino acid, or analogue or mimetic thereof. The presence of $A_x$ is required, however, as it has been found that compounds without $A_x$ show generally poor binding to P-selectin compared to similar compounds which comprise $A_x$. In one of the preferred embodiments, $A_x$ is a D- or L-amino acid selected from the group consisting of aspartic acid (D) and glutamic acid (E), or an analogue or mimetic thereof. In this embodiment, the characteristics of $A_x$ resemble those of $A_2$; this compound can be defined as comprising the sequence $XA_2A_3A_1A_2A_1Y$. It has to be noted, though, that the 2 units of $A_2$ (like the 2 units of $A_1$) are selected independently, i. e. they can be identical or different from each other.

X is defined as any N-terminal group or sequence. For example, X can simply be a hydrogen. More preferably, X is a sequence of one or more amino acids, or analogues or mimetics thereof. In one of the preferred embodiments, X comprises at least two amino acids. More preferably, X comprises an aspartic acid (D), preferably linked to $A_x$ via a spacer consisting of one other amino acid.

Y is defined as any C-terminal group or sequence. If no amino acids or analogues are comprised in Y, the C-terminal group may be a hydroxyl group. In a preferred embodiment, Y is a sequence of up to about five amino acid units. It is also preferred that at least one amino acid with a negatively charged side chain is present in Y, preferably being separated from the remaining $XA_xA_3A_1A_2A_1$ sequence by one to three amino acids. The recognition by P-selectin is more tolerant to substituents at the C-terminus than at the N-terminus. The skilled person is competent to find suitable amino acids in this respect.

The compound of the invention can possess a cyclic or otherwise constrained backbone. In that case, X+Y together may suitably be linked through a cys-cys binding, although, of course, also other types of (chemical) linkages can be present, such as an amide binding, a thioether binding, a carbamate binding or an ester binding.

The length of the group X+Y is not particularly critical as long as the core sequence is recognised by P-selectin. Generally, the minimum length of X+Y corresponds with the length of 5-6 amino acids.

In one of its embodiments, the invention provides compounds which possess, in addition to the structural characteristics set forth above, a unit $A_4$ at the C- or N-terminal end, wherein $A_4$ is a D- or L-amino acid with a hydrophilic side chain, or an analogue or mimetic thereof. Preferably, $A_4$ is serine (S), glycine (G), lysine (K), arginine (R), or glutamic acid (E). Most preferred is serine (S). A preferred position for $A_4$ is between Y and the remaining part of the sequence, as represented by the sequences $XA_xA_3A_1A_2A_1A_4Y$ and $XA_2A_3A_1A_2A_1A_4Y$.

Compounds of the invention possess linear, branched, cyclic, or constrained backbones. For instance, peptides or functional equivalents with at least two cysteine (C) units can be cyclized by oxidation. If a compound is cyclized via such a disulfide bond, it is preferred that the participating cysteine units are members of X and Y, respectively. Cyclic structures are, in fact, an example for conformationally constrained backbones. Other types of constrained structures may also be introduced to decrease the conformational flexibility of the compound. Especially the presence of olefinic bonds or small ring structures in the backbone serve this purpose. Examples of such constraints are given in Pharmaceutical Biotechnology, Ed. D. J. A. Crommelin and R. D. Sindelar, Harwood Academic Publishers, 1997, p. 139f.

In one of the preferred embodiments, the compounds of the invention are provided as multimers of peptides or functional equivalents. As used herein, multimers, which in peptide chemistry are also called oligomers, refer to peptides, proteins, peptoids, peptidomimetics, or analogues thereof, which are composed of more than one peptide chain. For example, tetramers of biotinylated peptides comprising the sequence $XA_xA_3A_1A_2A_1Y$ were found to possess a substantially higher affinity to P-selectin than the peptides they were composed of Preferred multimers of the invention have an affinity constant for P-selectin of below $1/20$, and especially below $1/100$ of the affinity constant of the corresponding peptides.

In another type of multimer that can be created to form the compounds of the invention, single peptide or peptoid chains are coupled to a biocompatible protein, such as human serum albumin, humanized antibodies, liposomes, micelles, synthetic polymers, nanoparticles, and phages. Multimers can also represent peptide sequences which are serially coupled to each other via spacers, i.e. concatamers, or dendrimers, or clusters.

The compounds can generally be prepared by the methods that are known for the preparation of peptides and similar substances. Smaller compounds containing only a few amino acids or similar units, and preferably not more than 30-50 units, can be prepared by chemical or enzymatic ligation techniques, either using the classical approach in which the reactions take place in solution or suspension, or by employing the more modern solid phase approach, in which the peptide is assembled while being anchored to a solid surface, such as a polymeric bead. Larger compounds are typically synthesized by automatic solid phase peptide synthesizers.

Alternatively, the compounds can be prepared by known genetic engineering techniques. This approach is especially valid if the compound is indeed a peptide or a slightly modified peptide. For instance, a DNS sequence which encodes the compound can be associated or combined with an expression vector capable of transfecting cells. In another step of the method, host cells or target cells are transfected with said DNA by contacting the cells with the vector and the vector-associated DNA under conditions which allow transfection. In a further step, the host or target cells are cultured under conditions which allow the expression of the compound. Subsequently, the compound can be isolated. If the compound itself cannot be encoded or expressed but is very similar to a peptide that can be encoded or expressed, the method can be applied to prepare the peptide to which the compound is similar, followed by one or more steps in which the peptide is modified by chemical or enzymatic techniques to prepare the compound.

Various types of vectors are used for this purpose, such as viral vectors, lipoplexes, polyplexes, microspheres, nanospheres, dendrimers, naked DNA, peptide delivery systems, lipids, especially cationic lipids, or liposomes made thereof, polymeric vectors, especially those made of polycationic polymers. Among the preferred viral vectors are retroviruses, adenoviruses, adeno-associated viruses, herpes simplex viruses, and virosomes. Preferred non-viral vectors include chitosan, SPLP, polymeric systems based on PLGA, polyethyleneimines, polylysines, polyphosphoamidates, poly(meth)acrylates, polyphosphazenes; DOPE, DOTAP, and DOTMA.

Some more comprehensive summaries of methods which can be applied in the preparation of the compounds are described in: W. F. Anderson, Nature 392 Supp., 30 Apr. 1998, p. 25-30; Pharmaceutical Biotechnology, Ed. D. J. A. Crommelin and R. D. Sindelar, Harwood Academic Publishers, 1997, p. 53-70, 167-180, 123-152, 8-20; Protein Synthesis: Methods and Protocols, Ed. R. Martin, Humana Press, 1998, p. 1-442; Solid-Phase Peptide Synthesis, Ed. G. B. Fields, Academic Press, 1997, p. 1-780; Amino Acid and Peptide Synthesis, Oxford University Press, 1997, p. 1-89.

Salts of peptides or functional equivalents are prepared by known methods, which typically involve the mixing of the peptide or peptoid with either a pharmaceutically acceptable acid to form an acid addition salt, or with a pharmaceutically acceptable base to form a base addition salt. Whether an acid or a base is pharmaceutically acceptable can be easily decided by a person skilled in the art after taking the specific intended use of the compound into consideration. For instance, not all acids and bases that are acceptable for in vitro diagnostic compositions can be used for therapeutic compositions. Depending on the intended use, pharmaceutically acceptable acids include organic and inorganic acids such as formic acid, acetic acid, propionic acid, lactic acid, glycolic acid, oxalic acid, pyruvic acid., succinic acid, maleic acid, malonic acid, cinnamic acid, sulfuric acid, hydrochloric acid, hydrobromic acid, nitric acid, perchloric acid, phosphoric acid, and thiocyanic acid, which form ammonium salts with free amino groups of peptides and functional equivalents. Pharmaceutically acceptable bases, which form carboxylate salts with free carboxylic groups of peptides and functional equivalents, include ethylamine, methylamine, dimethylamine, triethylamine, isopropylamine, diisopropylamine, and other mono-, di- and trialkylamines, as well as arylamines. Moreover, also pharmaceutically acceptable solvates, complexes or adducts, such as hydrates or ethurates are encompassed.

Multimers can, for example, be prepared by biotinylating the N-terminus of peptide or peptoid chains and subsequent complexation with streptavidin. As streptavidin is able to bind 4 biotin molecules or conjugates with high affinity, very stable tetrameric peptide complexes can be formed by this method. Multimers may be composed of identical or different peptides or functional equivalents. Preferably, however, the multimers of the invention are composed of two or more identical peptides or functional equivalents.

A further aspect of the invention refers to the uses of the disclosed compounds. Since the compounds bind selectively to P-selectin, they can, depending on their type of interaction with p-selectin after binding, function as antagonists, partial antagonists, or as mere targeting means to target conjugated substances to cells and tissues expressing P-selectin. Thus, the compounds can be advantageously used in pharmaceutical compositions. According to the invention, such pharmaceutical compositions are provided as well.

As used herein, the term "pharmaceutical composition" refers to therapeutic and diagnostic compositions, as well as to medicaments and diagnostics containing such compositions. Therapeutic compositions and medicaments are used for the prevention or treatment of diseases and other conditions of mammals whose improvement is desirable. Diagnostics and diagnostic compositions are used for the diagnosis of such diseases in vivo and in vitro.

A preferred use of the compounds is for preparing therapeutic compositions or medicaments to prevent or improve diseases and conditions involving the adhesion of leukocytes, such as monocytes and neutrophils, to the vascular endothelium and to platelets, and further involving platelet aggregation. The compounds can also be used in compositions for treating diseases in which the inhibition of P-selectin-mediated intracellular signaling is desirable.

For instance, compositions containing one or more compounds of the invention can contribute to controlling leukocyte-mediated inflammatory processes. It is known that activated leukocytes release toxic molecules which can damage normal tissue. These inflammatory responses, some of which also involve P-selectin-mediated platelet activation, are part of several pathological conditions, such as transplant rejection, cold ischemia, hemorrhagic shock, septic shock, tumor metastasis, chronic inflammation, rheumatoid arthritis, inflammatory bowel disease, atherosclerosis, restenosis, angiogenesis, disseminated intravascular coagulation, adult respiratory stress syndrome, circulatory shock, severe traumatic brain injury, relapsing-remitting multiple sclerosis, cerebral artery occlusion, ischemia, stroke, acute myocardial infarct, arterial injury, such as produced by angioplasty, myocardial ischemia, renal injury from ischemia and reperfusion, and renal failure.

In another embodiment, the compounds are used in the preparation of diagnostic compositions or products. Such compositions can be used for in vitro tests to quantify P-selectin concentrations in body fluids as markers for the diseases and conditions described above. They may be also used for in vivo diagnostic imaging procedures to monitor P-selectin mediated atherosclerosis, aneurisms, restenosis following percutaneous transluminal coronary angioplasty (post-PTCA restenosis), and other conditions selected from those in which P-selectin is mobilized. As an option for this use, a compound according to the invention may be conjugated with a chelator, which is subsequently complexed with an isotropic label that is detectable by the chosen monitoring system.

Another use of the compounds is as that of a tool in research. For instance, they can be used to test the binding affinity of molecules to P-selectin or functional equivalents of P-selectin. To conduct this test method, P-selectin or a functional equivalent of P-selectin would be contacted and incubated with a molecule to be tested for binding affinity and with a compound of the invention. A reduced binding of the compound of the invention would indicate an affinity of the molecule to P-selectin.

It has also been found by the inventors that P-selectin may be cleaved by naturally occurring members of the calpain family. Interestingly, some of the proteases of the calpain family seem to be the only natural polypeptide structures that comprise one of the preferred peptide sequences of the compounds of the invention, which is the core motif EWVDV. The overactivation of calpain 1 and calpain 2 is most likely associated with neurological diseases such as Alzheimer's disease, traumatic brain injury. stroke, and cataracts. Calpain 3 activity may be involved in some types of muscular dystrophy, that of calpain 9 in gastric cancer, while the calpains 8 and 10 seem to play a role in type 2 diabetis mellitus. Further aspects of the involvement of the calpains in various human diseases are described by Y. Huang and K. Wang in a review article, The calpain familiy and human disease, Trends Mol. Med. 7, 355-362, 2001, which is incorporated herein by reference.

Furthermore, it has been found that the compounds of the invention can inhibit the cleavage of L-selectin and P-selectin induced by calpain, with a much higher affinity—typically about 100 fold—for P-selectin. From a mechanistic point of view, this suggests that calpain is involved in the activation of the selecting. More in particular, the shedding of the selectins from the surfaces of the cells in which they are expressed may be induced by calpain. Consequently, the compounds of the invention are useful for any applications in which it is desirable to inhibit the interaction between P-selectin and calpain.

The compounds can also be used as targeting molecules or conjugates in pharmaceutical compositions for the targeting of drugs or genetic material to tissues that express P-selectin. As conjugates, the compounds can be directly coupled with active molecules or nucleic acids that are to be delivered to such tissues. Alternatively, they can be incorporated into or anchored onto the surface of liposomes or other lipid vesicles, emulsion droplets, polymers, nano- or microparticles to obtain targeted vehicles for drugs or genetic material which is delivered to P-selectin expressing tissues.

The pharmaceutical compositions preferably contain one or more compounds with P-selectin affinity as disclosed herein and at least one carrier or excipient. As used herein, a carrier or excipient is any pharmaceutically acceptable substance or mixture of substances having no substantial pharmacological activity, which can be used as a vehicle or as an auxiliary substance to formulate a compound into dosage form which is stable and easy to administer. Examples of pharmaceutically acceptable excipients are found in the monographs of all major pharmacopoeias.

In one embodiment, the composition is formulated and processed for parenteral injection, preferably for intravascular injection, such as intravenous or intra-arterial, but also for intramuscular, subcutaneous, intralesional, intraperitoneal or other routes of parenteral administration. The same principles that govern the formulation of other drugs for these administration routes will also teach those skilled in the arts on how to prepare such compositions. For instance, one of the requirements of parenteral dosage forms is their sterility. Other requirements are described in all major pharmacopoeias, such as in USP 24, in the monograph "General Requirements for Tests and Assays. 1. Injections", p. 1775-1777. To increase the stability of a parenteral formulation, it may be necessary to provide a dried dosage form which must be reconstituted before it can be administered. An example of such a dosage form is a freeze-dried or lyophilized formulation.

It may be desirable to administer a compound of the invention as a parenteral controlled release dosage form to avoid frequent injections and to improve the effectiveness and convenience of the therapy. Various methods of preparing such depot formulations are known. Prolonged release may be provided by solid implants, nanoparticles, nanocapsules, microparticles, microcapsules, emulsions, suspensions, oily solutions, liposomes, or similar structures.

Excipients that are particularly useful for the preparation of parenteral formulations are solvents, cosolvents and liquid or semisolid carriers, such as sterile water, ethanol, glycerol, propylene glycol, polyethylene glycol, butanediol, fatty oils, short- and medium chain triglycerides, lecithin, polyoxyethylene castor oil derivatives; substances to adjust the osmolality and pH, such as sugars, especially glucose, sugar alcohols, especially mannitol, sodium chloride, sodium carbonate, citric acid, acetate, phosphate, phosphoric acid, hydrochloric acid, sodium hydroxide etc.; stabilizers, antioxidants, and preservatives, such as ascorbic acid, sodium sulfite or -hydrogen sulfite, EDTA, benzyl alcohol etc.; other excipients and lyophilization aids, such as albumin, dextran etc.

Alternatively, the pharmaceutical compositions may be designed for oral administration and processed accordingly. Appropriate oral dosage forms include tablets, hard capsules, soft capsules, powders, granules, orally disintegrating dosage forms, syrups, drops, suspensions, effervescent tablets, chewable tablets, oral films, lyophilized dosage forms, sustained release dosage forms, controlled release dosage forms. In one of the preferred embodiments, the oral dosage form is an enterically coated solid dosage form to provide protection of the compound from the acidic and proteolytic environment of the stomach.

It may also be advantageous to administer a compound of the invention in a transmucosal dosage form. This route of administration is non-invasive and patient-friendly; at the same time it may lead to an improved bioavailability of the compound compared to oral administration, especially if the compound is not stable in the fluids of the digestive system, or if it is too large to be absorbed from the gut effectively. Transmucosal administration is possible, for instance, via nasal, buccal, sublingual, gingival, or vaginal dosage forms. These dosage forms can be prepared by known techniques; they can be formulated to represent nasal drops or sprays, inserts, films, patches, gels, ointments, or tablets. Preferably, the excipients used for a transmucosal dosage form include one or more substances providing for mucoadhesion, thus prolonging the contact time of the dosage form with the site of absorption and thereby potentially increasing the extent of absorption.

In a further embodiment, the compounds are administered via the pulmonary route, using a metered dose inhaler, a nebulizer, an aerosol spray, or a dry powder inhaler. Appropriate formulations can be prepared by known methods and techniques. Transdermal, rectal, or ocular administration may also be feasible in some cases.

It can be advantageous to use advanced drug delivery or targeting methods to deliver a compound of the invention more effectively. For instance, if a non-parenteral route of administration is chosen, an appropriate dosage form may contain a bioavailability enhancing agent, which may be any substance or mixture of substances which increases the availability of the compound. This may be achieved, for instance, by the protection of the compound from degradation, such as by an enzyme inhibitor or an antioxidant. More preferably, the enhancing agent increases the bioavailability of the compound by increasing the permeability of the absorption barrier, which is typically a mucosa. Permeation enhancers can act via various mechanisms; some increase the fluidity of mucosal membranes, while others open or widen the gap junctions between mucosal cells. Still others reduce the viscosity of the mucus covering the mucosal cell layer. Among the preferred bioavailability enhancers are amphiphilic substances such as cholic acid derivatives, phospholipids, ethanol, fatty acids, oleic acid, fatty acid derivatives, EDTA, carbomers, polycarbophil, and chitosan.

In a further aspect, molecules capable of binding to the compounds disclosed above are within the scope of the invention. For instance, standard hybridyzation technology can be applied to prepare specific monoclonal antibodies to a compound. Other techniques are available to design and prepare smaller molecules capable of binding to a compound of the invention.

The following examples are intended to further illustrate the invention, but not to limit its scope to the embodiments presented herein.

EXAMPLE 1

The following peptides were prepared by solid-phase synthesis on an automatic synthesizer by standard Fmoc chemistry using HBTU/HOBt as activating agent:

```
          ......AₓA₃A₁A₂A₁
TM1:        C P E F V D V E G D P G A L L A C  (SEQ ID No. 3)
TM2:          C G W V D V I A S G D T A T L A C  (SEQ ID No. 4)
TM11:   C D V E W V D V S S L E W D L P C       (SEQ ID No. 5)
TM16:       C P D W V D V F K L V E G V M L C   (SEQ ID No. 6)
TM17: C L M G C W C D V G V G G E S L C         (SEQ ID No. 7)
SH31: V G L D P R D W V D V S D Y A             (SEQ ID No. 8)
SH32:           D W V D V R E V L T G E Q R V   (SEQ ID No. 9)
A17:        C D V E W V D V S C                 (SEQ ID No. 10)
A18:        C D V E W V D V S                   (SEQ ID No. 11)
A19:          D V E W V D V S                   (SEQ ID No. 12)
A27:          D V E W V D V A                   (SEQ ID No. 13)
```

The peptides were biotinylated by conjugating an Ahx linker to the N-terminus of each peptide sequence and subsequently coupling the conjugate to biotin. TM11 was also prepared in a cyclized configuration by oxidation, thus forming disulfide bonds between the N- and C-terminal cysteines. Tetramers of TM11 and SH31 were derived by incubation of 10 μM streptavidin with biotinylated peptide in a 1 to 4 molar ratio for 2 hours at room temperature (RT). The quality of the peptides was checked by Mass Spectroscopy and HPLC.

The affinity of the compounds to P-selectin was investigated by using an adapted ELISA method. Streptavidin-horseradishperoxidase (strepPO) was incubated with TM11-biotin in a 1 to 4 molar ratio for 2 hours at RT, hereby forming a tetrameric peptide strepPO-complex. For competition studies, microtiter wells were coated with chimeric human p-selectin as described for the isolation of p-selectin binding phage. Wells were then incubated with 2.5 nM TM11-strepPO complex in assay buffer for 1 hour at 4° C., in the presence of titered amounts of peptides to compete for binding to human p-selectin. Linear compounds were tested in the presence of DTT to prevent aggregate formation. After washing 6 times with assay buffer, the wells were incubated with 100 μl TMB/H$_2$O$_2$ for 15 min at RT. The reaction was stopped with 1 M H$_2$SO$_4$ and the absorbance read at 450 nm. From the results, the affinity constants were calculated:

|  | Affinity |
|---|---|
| Biotin-TM1: | 82 μM |
| Biotin-TM2: | 49 μM |
| Biotin-TM11: | 2 μM |
| Biotin-TM11(cyclic): | 2 μM |
| Biotin-TM16: | 12 μM |
| Biotin-TM17: | 7 μM |
| Biotin-SH31: | 19 μM |
| Biotin-A17: | 0.1 μM |
| Biotin-A19: | 12 μM |
| Tetrameric TM11: | 10.7 nM |
| Tetrameric SH31: | 61.3 nM |

The affinity of the compounds was confirmed by a cell adhesion assay in which Chinese hamster ovary cells expressing human P-selectin were incubated with HL60 cells expressing PSGL-1 in the presence of titered amounts of the compounds.

EXAMPLE 2

Comparative Example

The following compounds were prepared as in example 1 and tested for their affinity to human P-selectin. It should be noted that even though the compounds are very similar to the compounds of example 1, they do not fully meet the structural requirements of claim 1 and are therefore not compounds according to the invention:

|  | Affinity [μM] |
|---|---|
| D V E A V D V S (SEQ ID No. 14) | 400,000 |
| D V E W A D V S (SEQ ID No. 15) | 1,400 |
| D V E W V A V S (SEQ ID No. 16) | 21,000 |
| D V E W V D A S (SEQ ID No. 17) | 13,000 |
| E W V K V A (SEQ ID No. 18) | 13,000 |

EXAMPLE 3

Inhibition of Platelet Aggregation

The following compounds were prepared as described in Example 1 and tested for their effect of inhibition of platelet aggregation.

Human platelets were activated by ADV, and the extent of platelet aggregation was measured in the presence or absence of EWVDV (SEQ ID No: 19)-containing peptides. It was shown that DVEWVDVS (A19) (SEQ ID No: 12) and CDVEWVDVSC (A17) (SEQ ID No: 10) significantly impaired the second phase of platelet aggregation, with the aggregation reduced by about 45% and 25%, respectively.

EXAMPLE 4

Interaction of Compounds with Sulfatide Liposomes

The compounds below were prepared as described in Example 1 and tested for their interaction with liposomes carrying 22% of sulfatides. It should be noted that the interaction of the compounds with sulfatides is an additional and optional aspect of the activity of the compounds of the invention. Compounds not interacting with sulfatides may still represent compounds of the invention, as long as they bind to P-selectin and comprise the consensus motif as defined in claim 1.

Liposomes were prepared by sonication from egg yolk phosphatidylcholine, cholesterol, and sulfatides, all dissolved in chloroform/methanol (1:1, v/v), at weight ratios of 4:0.8:1.33. A tracer amount of [$^3$H]-cholesterol (1.3×108 dpm) was added, and the mixture was dried under a stream of nitrogen. The resulting lipid layer was vortexed in PBS and subsequently sonicated, resulting in liposomes with mean particle diameters of 59-62 nm.

Fc-specific goat anti-human IgG in coating buffer (50 mM NaHCO$_3$, pH 9.6) was incubated in a high binding 96 well plate. The next day, wells were washed with assay buffer (20 mM HEPES, 150 mM NaCl, 1 mM CaCl$_2$, pH 7.4) and incubated with blocking buffer (3% BSA in assay buffer). After washing, wells were incubated with human P-selectin-IgG, washed, and subsequently incubated with the [$^3$H]-cholesterol labeled liposomes in the presence or absence of the compounds below and antibodies for 2 hours at 4° C. After removal of unbound liposomes, bound liposomes were collected and counted using a scintillation counter.

It was found that the compounds DVEWVDVS (SEQ ID No: 12), DVEWVDVA (SEQ ID No: 13), and C DVEWVDVSC (SEQ ID No: 17), significantly inhibited the binding of sulfatides to P-selectin, whereas the compounds DVEAVDVS (SEQ ID No: 14) and EWVDV (SEQ ID No: 19) did not. It appears that, apart from the core sequence as defined above, the aspartic acid two positions outside the core sequence (D, underlined) was an essential feature for the effective inhibition of sulfatides.

The invention claimed is:

1. A peptide compound with affinity to human P-selectin of the sequence $XA_XA_3A_1A_2A_1Z$, or a pharmaceutically acceptable acid or base addition salt thereof, wherein:
   - each $A_1$ is independently a D- or L-cysteine (C), D- or L-methionine (M), or D- or L-valine (V);
   - $A_2$ is a D- or L-aspartic acid (D);
   - $A_3$ is a D- or L-phenylalanine (F) or D- or L-tryptophan (W);
   - $A_X$ is a D- or L- glutamic acid (E), D- or L-aspartic acid (D), D- or L-cysteine (C) or D- or L-glycine (G);
   - X marks the N-terminal side of said sequence and is a hydrogen or contains 1 to 6 D- or L-amino acid residues; and Z marks the C-terminal side of said sequence and is a hydroxyl or contains 1 to 11 D- or L-amino acid residues terminated by a hydroxyl, wherein X and Z together can form a cyclic system, provided that when the compound is cyclized by a Cys-Cys disulfide bond, each participating Cys residue is a member of X and Z respectively.

2. The compound according to claim 1, wherein said sequence further comprises an amino-acid residue $A_4$ at the N-terminal or C-terminal end, wherein
   $A_4$ is a D- or L-amino acid comprising a hydrophilic side chain and is selected from the group consisting of D- or L-serine (S), D- or L-glycine (G), D- or L-lysine (K), D- or L-arginine (R) and D- or L-glutamic acid (E).

3. The compound according to claim 1, wherein $A_X$ represents D- or L-glutamic acid (E) or comprises $A_2$.

4. The compound according to claim 1, wherein each $A_1$ is valine (V).

5. The compound according to claim 1, wherein $A_3$ is tryptophan (W).

6. The compound according to claim 1, wherein X comprises at least two amino acid residues, one of them being aspartic acid (D).

7. The compound according to claim 1, comprising a cyclic or constrained backbone structure.

8. A multimer, comprising at least two peptides according to claim 1, said multimer having an affinity constant for binding to P-selectin which is less than 1/20 of the affinity constant for binding to P-selectin as shown by each individual peptide of which the multimer is composed.

9. A composition comprising a compound according to claim 1 and one or more pharmaceutically acceptable carriers or excipients.

10. The composition according to claim 9, which is formulated and processed for parenteral administration.

11. The composition according to claim 9 which is formulated and processed for oral administration.

12. The composition according to claim 9 which is formulated and processed for transmucosal administration.

13. The composition according to claim 9, which is formulated and processed for pulmonary administration through a metered dose inhaler, a nebulizer, an aerosol spray dispenser, or a dry powder inhaler.

14. The composition according to claim 9 further comprising a drug targeting agent and/or a bioavailability enhancing agent.

15. The multimer according to claim 8, comprising at least two of said peptides, said multimer having an affinity constant for binding to P-selectin which is less than 1/100 of the affinity constant for binding to P-selectin as shown by each individual peptide of which the multimer is composed.

16. The composition according to claim 9 wherein the composition is formulated and processed for intravascular, intramuscular, subcutaneous, or intralesional injection.

17. The composition according to claim 9 wherein the composition is formulated and processed in form of a tablet, a capsule, granules, an enteric solid dosage form, a solid dosage form providing sustained or controlled release, or an orally disintegrating dosage form.

18. The composition according to claim 9 wherein the composition is formulated and processed for nasal, buccal, sublingual, or vaginal administration.

19. The compound according to claim 1, wherein
X is X'-D-AA-, wherein
   AA is a D- or L-amino acid; and
   X' marks the N-terminal side of said sequence and is a hydrogen or contains 1 to 4 D- or L-amino acid residues.

20. The compound according to claim 19, wherein AA is D- or L-valine.

21. A peptide compound with affinity to human P-selectin of the sequence $XA_XA_3A_1A_2A_1Z$, or a pharmaceutically acceptable acid or base addition salt thereof, wherein
   each $A_1$ is independently a D- or L-cysteine (C), D- or L-methionine (M), D- or L-valine (V);
   $A_2$ is a D- or L-aspartic acid (D);
   $A_3$ is a D- or L-phenylalanine (F) or D- or L-tryptophan (W);
   $A_X$ is a D- or L- amino acid;
   X marks the N-terminal side of said sequence and is a hydrogen; and
   Z marks the C-terminal side of said sequence and is a hydroxyl.

22. The compound according to claim 21, wherein
each $A_1$ is D-or L-valine (V) and
$A_3$ is D- or L-tryptophan (W).

* * * * *